(12) United States Patent
Sajo et al.

(10) Patent No.: US 6,761,679 B2
(45) Date of Patent: Jul. 13, 2004

(54) EMBEDDED RADIATION EMITTER FOR THE LOCALIZATION AND DOSIMETRY OF BRACHYTHERAPY SEED IMPLANTS

(75) Inventors: Erno Sajo, Baton Rouge, LA (US); Mark L. Williams, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 10/188,596

(22) Filed: Jul. 2, 2002

(65) Prior Publication Data

US 2004/0006255 A1 Jan. 8, 2004

(51) Int. Cl.[7] ................................................. A61N 5/00
(52) U.S. Cl. ................................................. 600/3; 600/1
(58) Field of Search ............................ 600/424, 427, 600/1–8

(56) References Cited

U.S. PATENT DOCUMENTS

| | | | | |
|---|---|---|---|---|
| 5,342,283 A | * | 8/1994 | Good | 600/8 |
| 6,099,457 A | * | 8/2000 | Good | 600/8 |
| 6,163,947 A | | 12/2000 | Coniglione | |
| 6,187,037 B1 | | 2/2001 | Satz | |
| 6,200,258 B1 | * | 3/2001 | Slater et al. | 600/8 |
| 6,333,971 B2 | * | 12/2001 | McCrory et al. | 378/162 |
| 6,503,186 B1 | * | 1/2003 | Cutrer | 600/8 |
| 6,549,802 B2 | * | 4/2003 | Thornton | 600/426 |

FOREIGN PATENT DOCUMENTS

| | | |
|---|---|---|
| WO | WO 97/19724 | 6/1997 |
| WO | WO 99/33063 | 7/1999 |

OTHER PUBLICATIONS

Bice, W.S. et al., "Source localization from axial image sets by iterative relaxation of the nearest neighbor criterion." Med. Phys., vol. 26(9), pp. 1919–1924 (1999).
Nath, R. et al., "Dosimetry of interstitial brachytherapy sources: Recommendations of the AAPM Radiation Therapy Committee Task Group No. 43." Med. Phys., vol. 22(2), pp. 209–234 (1995).
Roberson, P.L. et al., "Source placement error for permanent implant of the prostate." Medical Physics, vol. 24(2), pp. 251–257 (1997).
Willins, J. et al., "CT–based Dosimetry for Transperineal I–125 Prostate Brachytherapy," Int. J. Radiat. Oncol. Biol. Phy., vol. 39(2), pp. 347–353 (1997).

* cited by examiner

Primary Examiner—Samuel G. Gilbert
(74) Attorney, Agent, or Firm—André J. Porter; John H. Runnels; Bonnie J. Davis

(57) ABSTRACT

A device and method for improving the identification, localization, and dosimetry of brachytherapy seeds. The device is a brachytherapy seed comprising a therapeutic isotope and a marker isotope having an activity that is a fraction of the activity produced by the therapeutic isotope. The marker isotope emits positrons and/or photons capable of being imaged using radiation detection devices (e.g., positron emission tomography (PET), single-photon emission computed tomography (SPECT), gamma camera, computed tomography (CT)). The radiation dose of the marker isotope delivered beyond the immediate vicinity of the brachytherapy seed is low because the marker isotope is adapted to have an activity of at least one to two orders of magnitude lower than the activity of the therapeutic isotope. Thus, the presence of the marker isotope will not alter the therapeutic characteristics of the brachytherapy seed.

24 Claims, 5 Drawing Sheets

EMBEDDED RADIATION EMITTER FOR THE LOCALIZATION AND DOSIMETRY OF BRACHYTHERAPY SEED IMPLANTS

This invention pertains to the treatment of tumors, more particularly to a method for identifying, localizing, and measuring the dose delivered by brachytherapy seeds using imaging techniques.

Brachytherapy is a form of radiation treatment in which tiny pellets, commonly referred to as seeds, containing a radioactive material such as iodine-125 or palladium-103, are implanted within a tumor-containing tissue or organ. Brachytherapy allows the delivery of high doses of radiation to targeted tissues and organs, while limiting the radiation dose to neighboring normal (non-cancerous) tissues and organs.

Over the last few years, the use of permanent interstitial implants for treating carcinoma of the prostate has sharply increased, especially in early stages of the disease. When using permanent interstitial implants, the delivered dose of radiation and dose distribution within the target and neighboring organs depends on the accuracy of the brachytherapy source positioning. Often, implanted seed positions deviate from the optimal pattern developed in the treatment planning, primarily due to source positioning errors caused by inaccurate needle placement (depth and position), prostate motion, and seed splaying. See P. L. Roberson et al., "Source placement error for permanent implant of the prostate." *Medical Physics*, vol. 24(2), pp. 251–257 (1997).

Postoperative assessment of patient outcome and dosimetric descriptions of implants have relied on seed localization using computed tomography (CT), fluoroscopic images, magnetic resonance imaging (MRI), ultrasound imaging, or scanned radiographs. See J. Willins et al., "CT-based Dosimetry for Transperineal I-125 Prostate Brachytherapy," *Int. J. Radiat. Oncol. Biol. Phy.*, vol. 39(2), pp.347–53 (1997). Once imaging is complete, seed positioning and orientation are extracted from these images and used for three-dimensional reconstruction of the treatment area. Seed placement errors, doses, and dose volume histograms are determined post-operatively and correlated with pre-implant calculations. However, the resolution of these imaging methods and the resolution of subsequent seed localization are limited to approximately 5 mm. Problems include artifacts in the images, and the difficulties associated with localizing seeds across multiple CT planar images. See W. S. Bice et al., "Source localization from axial image sets by iterative relaxation of the nearest neighbor criterion." *Med. Phys.*, vol. 26(9), pp. 1919–1924 (1999). Furthermore, no existing method can provide implanted seed dosimetry without the prior localization of individual seeds.

Evaluating seed positions and resulting dose distributions is also encumbered by difficulties in target identification, and by volume changes in the implant area after implantation. See Willins et al. (1997). Some algorithms have been developed in the last decade (e.g., orthogonal film reconstruction, iterative relaxation, etc.) to automate seed identification and localization, based on various imaging methods (e.g., CT, fluoroscopic images, ultrasound images, MRI, etc.). However, despite increasingly sophisticated mathematical methods, algorithmic predictions have retained a high level of uncertainty. For example, a phantom study found that orthogonal film reconstruction techniques were able to locate only 66% of seeds within 5 mm of their actual location, while iterative relaxation methods in clinical studies had only a 72% success rate. See Bice et al. (1999).

The uncertainty in localizing low energy photon emitters (e.g., Pd-103), results in an unacceptable error when calculating doses from a brachytherapy seed to targeted or normal tissues. This error arises because the dose rapidly decreases within a few centimeters of the seed. See R. Nath et al., "Dosimetry of interstitial brachytherapy sources: Recommendations of the AAPM Radiation Therapy Committee Task Group No.43." *Med. Phys.*, vol.22(2), pp.209–234 (1995). For instance, for Pd-103 the dose fall-off along the radial transverse axis of the seed is approximately 25% for each 5 mm distance from the source. By comparison, I-125 has a dose fall-off rate of approximately 10% per 5 mm.

U.S. Pat. No. 6,187,037 describes a pre-calibrated, integral radiation device for vascular implantation that delivers site-specific therapy to prevent restenosis. The device comprises a tubular structure formed of bio-compatible metal that can be activated by irradiation or neutron bombardment, or by a proton or electron beam.

WO 99/33063 describes un-encapsulated palladium-103 brachytherapy sources produced by irradiating pre-formed rhodium metal or rhodium alloy seeds with protons from a charged particle accelerator.

U.S. Pat. No. 6,163,947 and WO 97/19724 describe a brachytherapy device for radiotherapy of interstitial malignant neoplasms or other radiation-treatable diseases. The device comprises a hollow tubular support having a hollow tube-shaped seed-substrate. Radioactive source material is deposited as a layer on the external surface of the device. In one embodiment, the radiation-emitting layer of the device may be prepared by plating the seed-substrate with a suitable non-radioactive isotope that may be transmuted in situ by neutron bombardment.

An unfilled need exists for a cost-effective device and method for improving cancer treatment by increasing the level of accuracy and convenience in dose determinations, and in identifying and localizing brachytherapy seeds.

We have discovered a reliable and inexpensive device and method to improve the dosimetry, identification, and localization of brachytherapy seeds. The novel brachytherapy source may be adapted, for example, to produce positron emissions. In one embodiment, a positron or gamma emitter is embedded as a marker in a brachytherapy seed and is then imaged using external radiation detection devices (e.g., positron emission tomography (PET), single-photon emission computed tomography (SPECT), gamma camera, etc., resulting in a new type of seed definition and localization, and direct dosimetry from the dose-volume data produced by radiological imaging software.

In another embodiment, the novel device and method provides a means for irradiating titanium seed capsules using protons, either before or after encapsulation, to produce V-48, which is a positron emitter. Irradiation after encapsulation also provides a means for producing both Pd-103 and V-48 in one step, avoiding the need for "hot-loading." ("Hot-loading" is the use of radioactive components during the manufacturing of brachytherapy seeds, which is more difficult and costly than using stable components during initial manufacturing.) Seeds produced with both Pd-103 and V-48 together in one step may have different dosimetric characteristics from those produced with a minute quantity of V-48 prepared separately from Pd-103. Such a situation may result if the contribution of the V-48 isotope to the total dose is non-negligible as compared to the contribution of Pd-103. The method described also provides a means for producing seeds with varying activity of positron emissions.

The invention provides a device and method for effectively identifying, localizing, and measuring the doses delivered by brachytherapy sources. The seed comprises a therapeutic isotope and a marker isotope capable of producing particle emissions, such as positrons or gamma photons. The activity of the marker is typically a fraction of that of the therapeutic isotope. Examples of suitable positron emitting markers include V-48, F-18, Na-22, Al-26, Sc-44, Mn-52, Fe-52, Co-56, Co-58, Ni-57, Ge-69, As-74, Rb-84, Zr-89, I-124, and Rh-99. Examples of suitable gamma emitting markers are Be-7, Co-57, Cu-67, Ga-67, Sr-82-Rb-82, Rb-83, Sr-85, Mo-99, Tc-99m. Optionally, the therapeutic and marker isotopes may be the same when the isotope, in addition to its therapeutic radiation, produces radiation of different types and/or energy that can be imaged by external detectors (e.g., Sr-82-Rb-82, In-111, In-115m, Sn-117m, Ba-135m, Dy-157, Pt-191, Pt-197m, Au-196, I-131, Ir-192). In which case the isotope will decay at two different rates, delivering therapeutic amounts of one form of ionizing radiation to tissue locally, in the vicinity of said device, and marker amounts of another form of radiation beyond the region in which the therapeutic radiation is delivered.

The novel technique has several advantages. First, when Pd-103 is used as a therapeutic isotope, the combination of Pd-103 and a marker isotope (e.g., V-48) may be manufactured with initially non-radioactive substances, which are subsequently transmuted by irradiation. Thus, costs are reduced compared to other methods of manufacturing brachytherapy seeds. Second, existing Ti-encapsulated seeds may be used in the novel process to generate a V-48 by transmutation. Practically no alterations to existing Ti-encapsulating processes are required, except for the subsequent irradiation step. Third, improved accuracy in seed identification, localization, and dosimetry can be achieved using this novel device with a positron emitter in the seed. In a preferred embodiment, the novel device utilizes V-48 as a positron emitter, capable of producing and emitting photons detectable using imaging devices such as PET, SPECT, or combinations. Fourth, V-48 (~16 days) and Pd-103 (~17 days) have similar half lives. Therefore, therapeutic usage and fabrication processes of seeds comprising both V-48 and Pd-103 are not obscured by decay mismatch.

In a preferred embodiment, the encapsulation material is natural titanium. Natural titanium is preferred because it produces V-48 after irradiation with high energyprotons or deuterons by undergoing $^{48}Ti(p,n)^{48}V$, $^{49}Ti(p,2n)^{48}V$, or $^{48}Ti(d,2n)^{48}V$ reactions. (The dominant isotope in natural titanium is $^{48}Ti$, which has a 73.8% abundance, while $^{49}Ti$ has a 5.5% abundance.)

Figure 1:
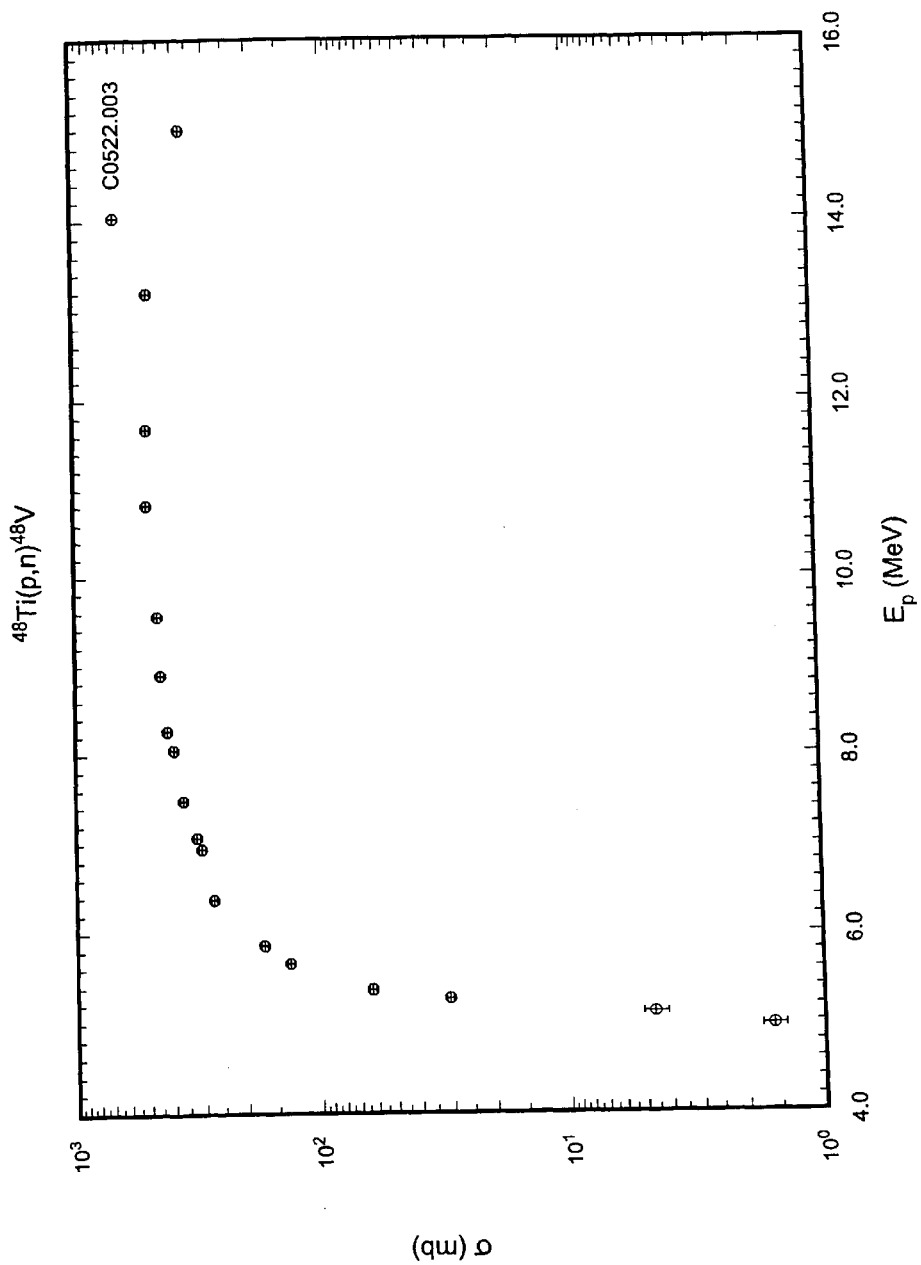
FIG. 1 is a graph plotting the threshold of proton energy and the cross-section of $^{48}$Ti(p,n)$^{48}$V.
Figure 2:
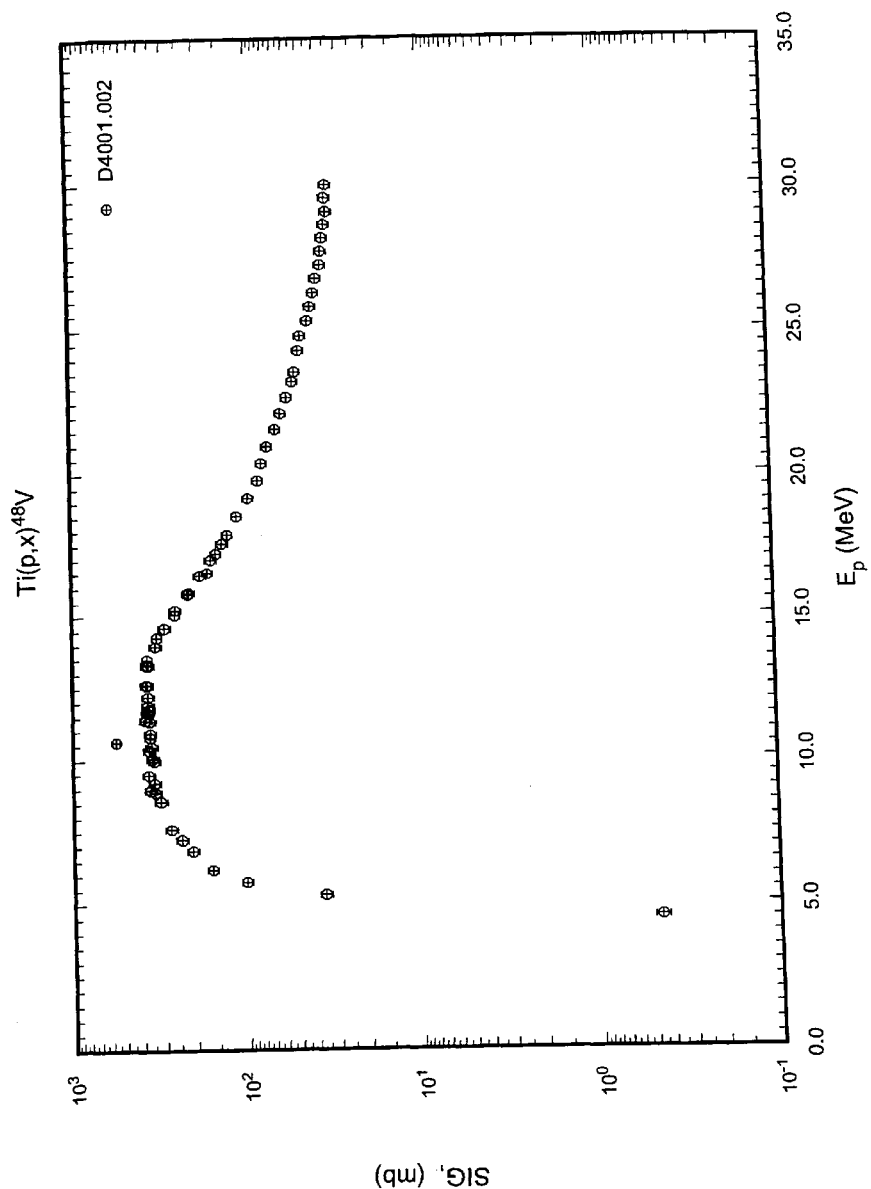
FIG. 2 is a graph plotting the cross-section for natural titanium undergoing a $^{nat}Ti(p,x)^{48}V$ reaction, as recommended by the National Nuclear Data Center (Brookhaven National Laboratory, N.Y.).

FIG. 1 depicts a comparison of proton energy versus cross-section for the $^{48}Ti(p,n)^{48}V$ reaction. The $^{48}Ti(p,n)^{48}V$ reaction has a threshold proton energy of approximately 4.8 MeV, and a maximum cross-section of 508 mb at a proton energy of about 11 MeV. See H. I. West et al., "Excitation functions for the nuclear reactions on titanium leading to the production of $^{48}V$, $^{44}Sc$ and $^{47}Sc$, by proton, deuteron and triton irradiations at 0–35 MeV." UCLR-ID-115738, November 1993, *Physical Review* C42 (1990) 683 (Data retrieved from the CSISRS database, file EXFOR C0522001 dated Jul. 26, 1999, National Nuclear Data Center, Brookhaven National Laboratory). The peak cross-section for natural titanium undergoing a $^{nat}Ti(p,x)^{48}V$ reaction is 386 mb at about 11.4 MeV. See FIG. 2. This cross-section was determined using 0.02 mm and 0.078 mm titanium foils, which are similar in thickness to those used in Ti-encapsulated brachytherapy seeds. See P. Kopecky et al., "Excitation functions of (p,xn) reactions on $^{nat}Ti$: monitoring of bombarding proton beams." *Applied Radiation Isotopes*, vol. 44, p. 687 (1993).

Other isotopes produced by the $^{nat}Ti(p,x)$ reaction either have short half lives (e.g., V-46 and V-47), or decay by low-energy photon emissions with low probabilities (e.g., V-49). All proton activation products of the $^{nat}Ti$ reaction decay by positron emissions and electron capture, resulting in a stable titanium end-product. Of the many possible positron emitters produced from the $^{nat}Ti$ reaction, V-48 has particularly desirable properties (e.g., half life and particle emission products) to be used in combination with Pd-103, and it has the lowest positron endpoint energy among the $^{nat}Ti(p,x)$ products. Half lives and particle emission products of V-48 and P-103 are shown in Table 1.

TABLE 1

| | Emission Energies (E) of V-48 Half Life: 15.971 days | | | Emission Energies (E) of Pd-103 Half Life: 16.961 days | | |
|---|---|---|---|---|---|---|
| Positron | E max | E ave | Probability | E max | E ave | Probability |
| | 0.69738 | 0.29140 | 0.50100 | — | — | — |
| Beta | — | — | — | — | — | — |
| Electrons and Photons | Energy (MeV) | | Probability | Energy (MeV) | | Probability |
| Electrons | 0.000420 | | 0.735540 | 0.002390 | | 0.907710 |
| | 0.004000 | | 0.348470 | 0.017000 | | 0.165760 |
| Photons | 0.000450 | | 0.001548 | 0.002700 | | 0.047774 |
| | 0.004505 | | 0.028901 | 0.020074 | | 0.198430 |
| | 0.004511 | | 0.057344 | 0.020216 | | 0.377240 |
| | 0.004930 | | 0.011471 | 0.022700 | | 0.117440 |
| | 0.511000† | | 1.002000 | 0.359610 | | 0.000308 |
| | 0.803230 | | 0.001500 | | | |
| | 0.928320 | | 0.007700 | | | |
| | 0.944100 | | 0.077600 | | | |
| | 0.983500 | | 1.000000 | | | |
| | 1.312100 | | 0.975000 | | | |
| | 1.437300 | | 0.001200 | | | |
| | 2.240300 | | 0.024100 | | | |
| | 2.361500 | | 0.000270 | | | |

†The 0.51100 MeV gamma line is due to positron annihilation. D.C. Kocher, "Radioactive decay data tables." DOE/TIC-11026, Technical Information Center, U.S. Department of Energy, Washington, D.C. (1981).

Neither the fabrication process nor the therapeutic use of seeds containing a combination of V-48 and Pd-103 is obscured by decay mismatch, since the difference in half lives between V-48 and Pd-103 isotopes is relatively small (~16 days versus ~17 days). In a preferred embodiment, the dose delivered to the targeted tissue by the positron emitter is at least an order of magnitude smaller than the dose generated by the Pd-103. (The therapeutic activity of a typical Pd-103 seed is approximately 1.6 mCi. The activity required for a PET scan to detect annihilation photons generated by the V-48 positron emission is in the $\mu$Ci range.) Low energy X-rays (4.56 keV on average, with a combined probability of 0.0977) and electrons produced by V-48 have a non-negligible dosimetric effect only in the immediate vicinity of the combined Pd-103 and V-48 seed. The range of this effect is mainly restricted to the residual range of the electrons that have traversed the seed encapsulation or are borne therein, in addition to electrons from photon interactions in the tissue. Dose deposition due to higher energy photons in the MeV range will be limited by the low activity of the V-48 in the seed, as shown in Example 1 below. Thus, V-48 will have a third order contribution to the combined dose of Pd-103 and V-48 due to its low activity and low emission probability at low energies. (I.e., the V-48 photons will generate a dose approximately two to three orders of magnitude lower than that from the therapeutic Pd-103. Thus, the presence of this isotope does not substantially alter the therapeutic characteristics of the seed.) Although the $^{nat}$Ti(p,x) reaction yields some V-49, its near-field dosimetric effect is also insignificant due to its low-energy photon emission (approximately 4.56 keV on average, with a combined probability of 0.195), and it is produced in a nuclear number density nearly ten times lower than that of V-48. When compared to Pd-103, the dose contribution of V-49 is of fourth order significance.

EXAMPLE 1

Dose Calculations

Figure 3:
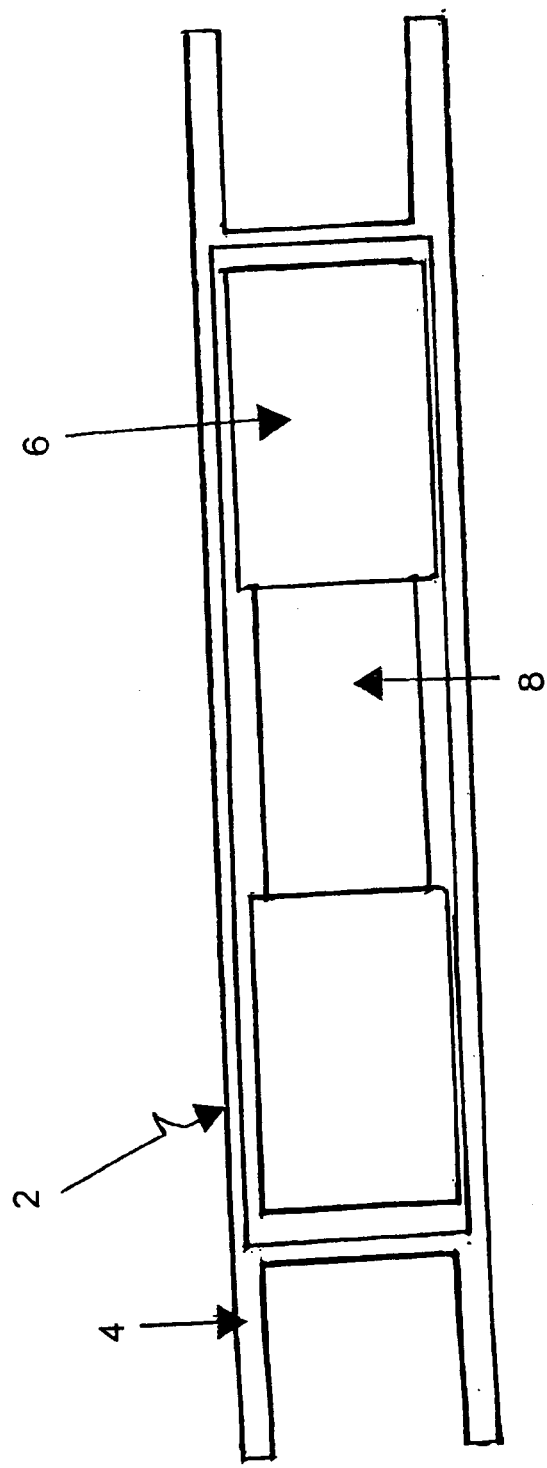
FIG. 3 illustrates a cross-sectional view of a brachytherapy seed in accordance with the present invention.

FIG. 3 shows the geometry of a brachytherapy seed 2, such as TheraSeed® Pd-103 (Theragenics Corporation, Buford, Ga.), used to conduct computer simulations to confirm that the projected dose delivered beyond the immediate vicinity of the seed is negligible when using V-48 in trace quantities of 1 µCi or less. Brachytherapy seed 2 comprises a capsule 4, pellet 6, and a radio-opaque marker 8. Capsule 4 was made of 0.8 mm dia. titanium tubing having a wall thickness of approximately 0.08 mm and a length of 4.5 mm. Two graphite pellets 6, plated with Pd-103, were inserted into capsule 4 to produce therapeutic activity. Graphite pellets 6 have an approximate length of 1 mm and a diameter of 0.6 mm. Marker 8 was placed between graphite pellets 6 to allow detection by CT scans or other imaging methods (e.g., fluoroscopicimages, magnetic resonance imaging (MRI), and ultrasound imaging). (The actual composition of marker 8 is proprietary; however, it is believed that said marker 8 comprises lead or tungsten.) Dimensions and material composition data forbrachytherapy seed 2 were obtained from the TheraSeed® manufacturer (Indigo Medical, a Johnson and Johnson Company, Cincinnati, Ohio).

Monte Carlo computer simulations were conducted, using brachytherapy seed 2, to calculated the projected dose delivered beyond the immediate vicinity of the seed when V-48 is used in trace quantities. (Monte Carlo calculations simulate the stochastic nature of energy deposition by nuclear radiation and are widely used in medical physics. Most modern brachytherapy seed designs are based on such calculations.) Coupled photon-electron simulations of energy depositions from V-48 and Pd-103 were performed to compute projected dose levels delivered within a 5 cm radius of the source, and throughout the entire human body, as described by the International Commission for Radiological Protection. The MCNP4b2 computer code was used to perform the Monte Carlo simulations. MCNP4b2 is a general Monte Carlo N-particle transport code which uses a condensed history method and physics approximations to determine dose depositions. (MCNP4b2 may be obtained from the Radiation Safety Information Center, Oak Ridge National Laboratory, Oak Ridge, Tenn.) Photon track length, kinetic energy released in matter ("kerma"), and energy deposition were calculated in ten ring detectors placed 5 mm apart from each other along the radial transverse axis of the seed. Photon track length and kerma estimators were used for the whole-body dosimetric calculations. Results were then compared to each other and to the radial dose function of Pd-103 seeds reported by Nath et al. (1995).

Figure 4:
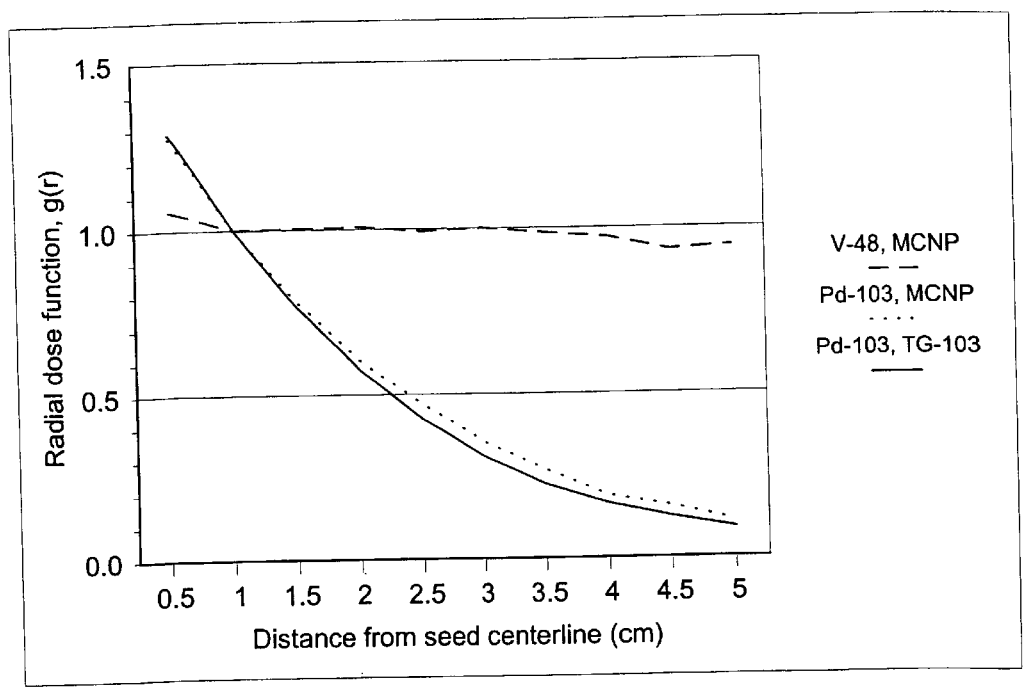
FIG. 4 illustrates a comparison of the radial dose functions of V-48 and Pd-103, as a function of the distance from the seed centerline.

FIG. 4 depicts comparisons of the radial dose functions of V-48 and Pd-103 within 5 cm from the source. The radial dose functions indicate the rate at which dose deposition changes with distance from the source. These functions were calculated based on the results of the MCNP4b2 computations, following the protocol of Nath et al. (1995). Monte Carlo computations for the Pd-103 and V-48 dose fall-off rates indicated that, due to its significantly higher energies, the V-48 dose per source particle (normalized at 1 cm from the source) varies from 70% of the dose produced by Pd-103, near the source (1 mm from the seed's centerline), to 800% far away from the source (approximately 5 cm from the seed's centerline). More specifically, the ratio of normalized doses per emitted particle generated between V-48 and Pd-103 is 0.7 near the surface of the seed (1 mm from the seed's centerline), and 8.0 at approximately 5 cm from the centerline. Additionally, the radial dose function of V-48 is essentially flat within the computational domain. However, the V-48 contribution to the therapeutic dose is negligible when V-48 is used in trace quantities as proposed. In fact, Monte Carlo dose computations for the entire human body showed that the dose due to the high-energy photons from trace quantities of V-48 is about 1% or less of that produced by Pd-103, when V-48 is used in trace quantities.

EXAMPLE 2

One-Step Production of Therapeutic and Marker Isotopes

To facilitate the one-step simultaneous production of a Pd-103 isotope and a V-48 tracer, the Pd-103 isotope is generated by a $^{103}$Rh(p,n)$^{103}$Pd reaction, while the V-48 is generated by a $^{nat}$Ti(p,x) reaction. The objective is to produce a Pd-103 activity about one to two orders of magnitude higher than the activity of the V-48 tracer. Current manufacturing processes for brachytherapy seeds such as TheraSeed® model 200 entail irradiating Pd-102 with thermal neutrons to produce Pd-103 through the $^{102}$Pd(n,γ)$^{103}$Pd reaction. This step is followed by chemical purification and plating of the Pd-103 on graphite pellets, and then hot-loading the graphite pellets into titanium capsules. See Nath et al. (1995).

In this embodiment of the invention, stable Rh-103 having an isotopic abundance of 100% is pre-loaded into a natural-abundance Ti capsule. Rh may be plated onto graphite pellets or onto other suitable substrates that can support the isotope (e.g., carbon, beryllium-based compounds, or other low atomic weight elements), in addition to avoiding interference with the therapeutic dose delivery. The Ti capsule and the Rh-103 are then irradiated with a proton beam. The proton beam energy and the wall thickness of the Ti capsule are adapted to achieve a low V-48 isotope activity level, while producing a high Pd-103 activity. To illustrate, the stopping power and particle range for 4.5 MeV protons normally incident on a 0.05 mm Ti foil were calculated using the PSTAR code, provided by the National Institute of Standard and Technology. The PSTAR computer code calculates stopping-power and range tables for protons in various elements and compounds (e.g., titanium, water, graphite, hydrogen, and helium). The calculated particle range for 4.5 MeV protons, using a continuous slowing down approximation, was 0.111 mm (approximately twice the thickness of the Ti foil). The residual energy of the protons leaving the foil and incident on the Rh target was 3.3 MeV. The microscopic cross-section ratios between Ti and Rh at 4.5 and 3.3 MeV, respectively, were approximately 6.6 (using experimental data reported by J. P. Blaser et al., "Anregungsfunctionen und Wirkungsquerschnitte der (p,n)-Reaktion (II)," *Helv. Phys. Acta.*, vol. 24, p. 441 (1951) and Kopecky et al. (1993), and 2.0 (using experimental data reported by C. H. Johnson et al., "Cross sections for (p,n) reactions in intermediate-weight nuclei." *Report, Oak Ridge National Laboratory*, ORNL-2910, p. 25 (1960)), respectively. By comparison, the macroscopic reaction cross-section ratios, using the reported data, were 8.5 and 2.5, respectively.

Figure 5:
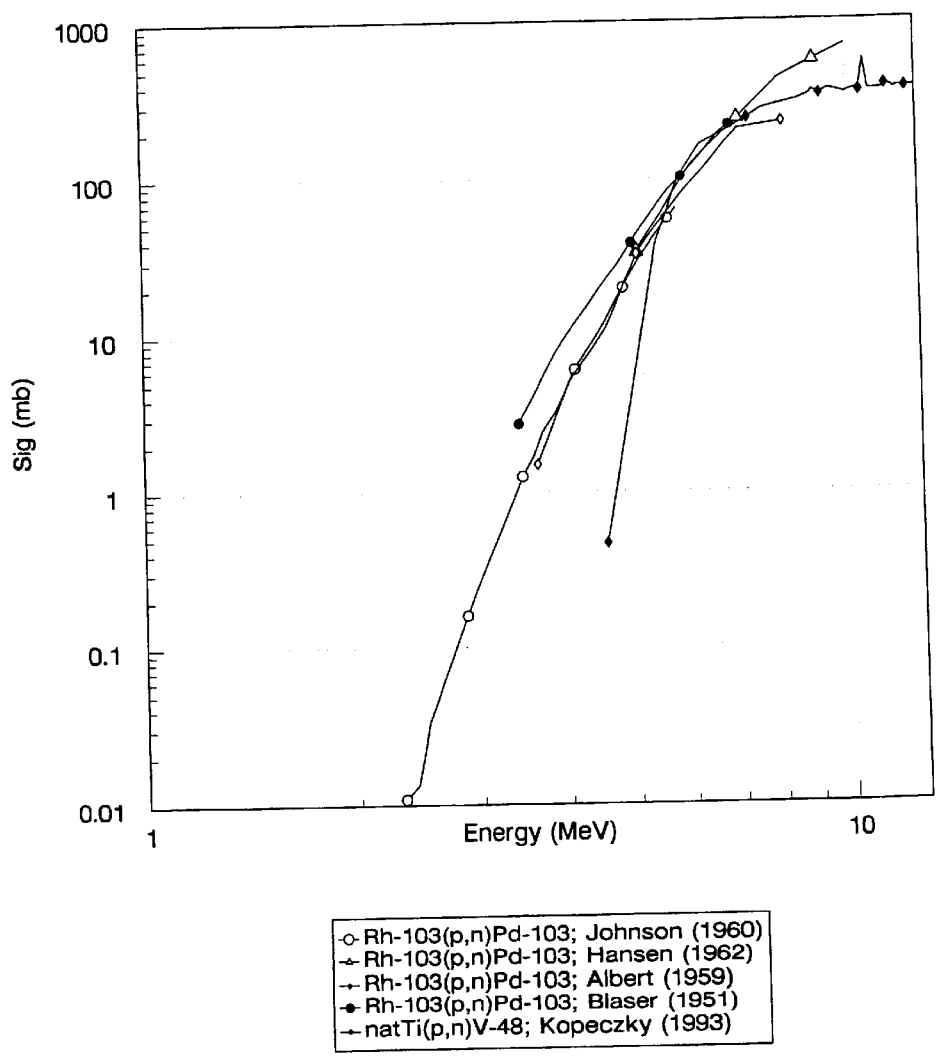
FIG. 5 illustrates the relative differences in cross-sections between Rh-103 (p,n) and $^{nat}Ti(p,x)$.

In a preferred embodiment, encapsulation wall thickness and proton energies relative to the (p,n) cross-sections of Ti and Rh are adapted to produce a Pd-103 activity of about one to two orders of magnitude higher than the activity of the V-48 tracer. In order to maintain the low activity of the V-48, the proton beam energy should be capable of taking advantage of the relative differences between the (p,n) cross-sections of Ti and Rh. The largest relative differences between the Rh-103 (p,n) and $^{nat}$Ti(p,x) cross-sections exist at energies ranging from approximately 4.5–5.5 MeV, and above 7 MeV. See FIG. 5. At these ranges, the cross-section of the $^{103}$Rh(p,n)$^{103}$Pd reaction substantially exceeds the cross-section of the $^{nat}$Ti(p,x)$^{48}$V reaction. For example, at 4.5 MeV proton energy, the $^{nat}$Ti cross-section is 0.46 mb, while the cross-section of Rh-103 is 12.4 mb. See Kopeczky et al. (1993) and Johnson et al. (1960), respectively. At 10 MeV the respective cross-sections are 350 mb and 703 mb. See Kopeczky et al. (1993) and L. F. Hansen et al., "Statistical theory predictions for 5 to 11 MeV (p,n) and (p,p') nuclear reactions in V-51, Co-59, Cu-63, Cu-65, and Rh-103." *Phys. Rev.*, vol. 128, p.291 (1962), respectively. Thus, the proper selection of proton energy, Ti wall thickness, and Rh target mass, as previously mentioned, could generate a range of activity ratios between V-48 and Pd-103 that would meet the desired balance of therapeutic versus imaging effectiveness.

A preferred ratio of macroscopic cross-sections of 10 or greater will produce a V-48 activity about one to two orders of magnitude lower than that of Pd-103 in the one step process, as shown in Example 2. However, the flux needed to generate 1 mCi of Pd-103 activity, when using 4.5 MeV protons incident on the titanium seed capsule, traversing through a 0.05 mm wall and subsequently incident on a 1 mg of Rh-103, target is relatively high, on the order of $10^{15}$ per cm$^2$ per second. Therefore, this method of seed manufacturing may be easier to implement for sources with low therapeutic activity if the low activity of V-48 is to be maintained.

EXAMPLE 3

Positron Range Considerations

In another embodiment, a positron emitter can be placed inside a seed encapsulation to act as a marker. Positron emitters and encapsulation or substrate material and thickness are adapted to optimize the resolution of the PET image-formation. (The encapsulation material is not limited to titanium.) In a preferred embodiment, the resolution is optimized by adapting the encapsulation or substrate material and thickness, and positron energy such that the capsule wall or substrate thickness equals or exceeds the positron range, without significantly shielding any generated annihilation photons. The range of positrons in the seed capsule will be less than that in tissue. For example, the range of positrons having 500 keV energy is approximately 2.5 mm in tissue, and less than 0.1 mm in titanium.

This method will optimize image resolution because the origins of the annihilation and source photons will be confined to the seed and will not extend into the surrounding tissue. When the origins of annihilation photons extend into the tissue, the resultant PET image will be blurred. However, when the annihilation photons are confined to the seed capsule, this blurring is reduced or eliminated. Additionally, the dosimetric characteristics of the seed will not change considerably because the positron emitter activity may be generated as needed, and only trace quantities are required in the seeds.

Many existing brachytherapy seeds that use Ti encapsulation may be converted into positron emitters at tracer levels, while retaining their therapeutic dosimetric characteristics, as shown in Examples 1 and 2. External irradiation of the encapsulation or the pre-manufactured seed by protons will yield V-48, which may be imaged using PET, PET with CT fusion, or other imaging means including high-resolution gamma cameras. In addition, other positron or gamma emitters may be embedded in encapsulated or pre-manufactured seeds and other seeds to serve as markers for the same purpose, as described in Example 3. Due to the short range of positrons in the high-atomic number encapsulation material, the location of the annihilation photon source will be very localized at the seed location, providing better resolution for image reconstruction.

The current resolution of image fusion between images from different techniques is in the range of 5 mm, when positrons annihilate in tissue. This includes range blurring and other inherent limitations. It is expected, however, that the new generation of lutetium oxyorthosilicate (LSO) based PET scanners and high-resolution gamma cameras equipped with multiple photomultiplier tubes will produce higher resolutions with enhanced image sharpness and contrast. Large gradients in activity, similar to the activity achieved by the positron emitter-marked brachytherapy seeds, have been shown to yield a resolution in the range of 2 mm or less when gamma cameras are used. These imaging techniques, coupled with numerical algorithms (e.g., orthogonal film reconstruction, iterative relaxation, etc.) that automate the task of seed identification and localization, will produce much better seed localization than currently available techniques that rely on software alone. In addition, PET technology allows the direct detemination of the dose delivered by seeds containing embedded positron emitters without the explicit knowledge of seed locations and orientations, by correlating the delivered dose to the dose inferred from the image reconstruction algorithm. Because PET or gamma camera imaging does not require a significant external radiation source, it is believed that this invention will also allow the localization of brachytherapy seeds during operations, allowing greater precision in initial implantation. This invention could replace or complement current techniques that primarily use trans-rectal ultrasound imaging for this purpose.

The complete disclosures of all references cited in this specification are hereby incorporated by reference. In the event of an otherwise irreconcilable conflict, however, the present specification shall control.

We claim:

1. A device for delivering ionizing radiation to mammalian tissue, comprising:
   (a) a therapeutic isotope that emits ionizing radiation suitable for treating neoplastic tissues; and
   (b) a positron emitting marker isotope capable of emitting identifiable radiation to allow detection of the location or dosimetry or both of said device;

wherein:
   (c) the size and shape of said device are adapted for insertion into mammalian tissue;

(d) the quantity, kind, and distribution of said therapeutic isotope in said device are adapted to deliver therapeutic amounts of ionizing radiation to tissue locally, in the vicinity of said device, but not to deliver substantial amounts of ionizing radiation to other parts of the body;

(e) the quantity, kind, and distribution of said marker isotope in said device are adapted not to deliver substantial amounts of radiation beyond the region in which said therapeutic isotope delivers substantial amounts of ionizing radiation;

(f) the quantity, kind, and distribution of said marker isotope in said device are adapted to emit a sufficient quantity and energy of radiation at a sufficient distance from said device that one or more radiation detectors external to the body can determine the location of said device, or can infer the dosimetry resulting from the therapeutic isotope as a function of the radiation detected from the marker isotope or both; and (g) said therapeutic isotope and said marker isotope are different.

2. A device as recited in claim 1, wherein said therapeutic isotope comprises Pd-103.

3. A device as recited in claim 1, wherein said marker isotope is selected from the group consisting of V-48, F-18, Na-22, Al-26, Sc-44, Mn-52, Fe-52, Co-56, Co-58, Ni-57, Ge-69, As-74, Rb-84, Zr-89, I-124, and Rh-99.

4. A device as recited in claim 1, wherein said marker isotope is V-48.

5. A device as recited in claim 1, further comprising a capsule for encapsulating said therapeutic isotope and said marker isotope.

6. A device as recited in claim 5, wherein said capsule comprises natural titanium.

7. A device as recited in claim 5, wherein said marker isotope is V-48.

8. A device as recited in claim 7, wherein said marker isotope is a part of said capsule for encapsulating said therapeutic isotope.

9. A device as recited in claim 1, wherein said radiation detector uses a fusion of computed tomography and positron emission tomography or single-photon emission computed tomography; wherein the images generated from both the computed tomography and the positron emission tomography or the single-photon emission computed tomography are combined.

10. A device as recited in claim 1, wherein said marker isotope generates a dose of radiation beyond the region in which said therapeutic isotope delivers substantial amounts of ionizing radiation at least approximately two to three orders of magnitude lower than that generated by said therapeutic isotope.

11. A device as recited in claim 1, wherein the location of said device can be determined at a range closer than about 5 mm using one or more radiation detectors external to the body.

12. A method for treating mammalian neoplastic tissue, comprising the steps of:

(a) introducing a device into or near the tissue comprising a therapeutic isotope and a positron emitting marker isotope; wherein the quantity, kind, and distribution of said therapeutic isotope in the device are adapted to deliver therapeutic amounts of ionizing radiation to tissue locally, in the vicinity of the device, but not to deliver substantial amounts of ionizing radiation to other parts of the body;

(b) allowing the device to remain in or near the tissue for a time sufficient to generate therapeutic ionizing radiation suitable for treating the neoplastic tissue; and (c) detecting radiation emitted by the positron emitting marker isotope using one or more radiation detectors external to the body, and inferring from the detected radiation the location or the dosimetry or both of the device.

13. A method as recited in claim 12, wherein the therapeutic isotope comprises Pd-103.

14. A method as recited in claim 12, wherein the marker isotope is selected from the group consisting of V-48, F-18, Na-22, Al-26, Sc-44, Mn-52, Fe-52, Co-56, Co-58, Ni-57, Ge-69, As-74, Rb-84, Zr-89, I-124, and Rh-99.

15. A method as recited in claim 12, wherein the marker isotope is V-48.

16. A method as recited in claim 12, further comprising the step of inserting the therapeutic isotope and the marker isotope into a capsule.

17. A method as recited in claim 16, wherein the capsule comprises natural titanium.

18. A method as recited in claim 16, wherein the marker isotope is V-48.

19. A method as recited in claim 18, wherein the marker isotope is a part of the capsule for encapsulating the therapeutic isotope.

20. A method as recited in claim 12, wherein the marker isotope generates a dose of radiation beyond the region in which the therapeutic isotope delivers substantial amounts of ionizing radiation at least approximately two to three orders of magnitude lower than that generated by the therapeutic isotope.

21. A method as recited in claim 12, wherein the radiation detector uses a fusion of computed tomography and positron emission tomography or single-photon emission computed tomography; wherein the images generated from both the computed tomography and the positron emission tomography or single-photon emission computed tomography are combined.

22. A method as recited in claim 12, wherein the therapeutic isotope and the marker isotope are different.

23. A method as recited in claim 12, wherein the therapeutic isotope and the marker isotope are the same.

24. A method as recited in claim 23, wherein the isotope is selected from the group consisting of V-48, Fe-52, As-74, I-124, Sr-82-Rb-82, In-111, In-115m, Sn-117m, Ba-135m, Dy-157, Pt-191, Pt-197m, Au-196, Au-198, I-131, and Ir-192.

* * * * *